United States Patent
Pan et al.

(10) Patent No.: US 6,342,079 B1
(45) Date of Patent: Jan. 29, 2002

(54) PRIMARY INTERMEDIATE FOR USE IN OXIDATIVE HAIR DYEING

(75) Inventors: Yuh-Guo Pan, Stamford; Mu-Ill Lim, Trumbull; Linas R. Stasaitis, Fairfield, all of CT (US)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 09/491,717

(22) Filed: Jan. 27, 2000

(51) Int. Cl.⁷ .......................... A61K 7/13; C07C 211/51
(52) U.S. Cl. .................. 8/410; 8/416; 564/305; 564/397; 564/418; 564/419
(58) Field of Search .............. 8/410, 416; 564/305, 564/397, 418, 419

(56) References Cited

U.S. PATENT DOCUMENTS

| 4,003,699 A | 1/1977 | Rose et al. .................... 8/10.2 |
| RE30,199 E | 1/1980 | Rose et al. .................... 8/10.2 |
| 4,840,639 A * | 6/1989 | Husemeyer et al. ............ 8/410 |
| 5,421,833 A | 6/1995 | Lorenz .......................... 8/410 |
| 5,538,516 A | 7/1996 | Cotteret et al. ................ 8/412 |
| 5,599,353 A | 2/1997 | Audousset et al. ............ 8/412 |

FOREIGN PATENT DOCUMENTS

| EP | 400331 B1 | 3/1993 | ............ A61K/7/13 |
| GB | 2239265 A | 6/1991 | ............ A61K/7/13 |

* cited by examiner

Primary Examiner—Margaret V. Einsmann
(74) Attorney, Agent, or Firm—Carmella A. O' Gorman; Charles J. Zeller

(57) ABSTRACT

1-(2,5-Diaminophenyl)ethanol useful as a primary intermediate for the oxidative dyeing of hair.

13 Claims, No Drawings

PRIMARY INTERMEDIATE FOR USE IN OXIDATIVE HAIR DYEING

FIELD OF THE INVENTION

This invention relates to a novel primary intermediate for use in hair coloring compositions comprising one or more oxidative hair coloring agents in combination with one or more oxidizing agents. The invention also relates to hair coloring compositions of this novel primary intermediate and to coloring or dyeing of hair using compositions containing this primary intermediate.

BACKGROUND OF THE INVENTION

Coloration of hair is a procedure practiced from antiquity employing a variety of means. In modern times, the most extensively used method employed to color hair is to color hair by an oxidative dyeing process employing hair coloring systems utilizing one or more oxidative hair coloring agents in combination with one or more oxidizing agents.

Most commonly a peroxy oxidizing agent is used in combination with one or more oxidative hair coloring agents, generally small molecules capable of diffusing into hair and comprising one or more primary intermediates and one or more couplers. In this procedure, a peroxide material, such as hydrogen peroxide, is employed to activate the small molecules of primary intermediates so that they react with couplers to form larger sized compounds in the hair shaft to color the hair in a variety of shades and colors.

A wide variety of primary intermediates and couplers have been employed in such oxidative hair coloring systems and compositions. Among the primary intermediates employed there may be mentioned p-phenylenediamine, p-toluenediamine, p-aminophenol, 4-amino-3-methylphenol, and as couplers there may be mentioned resorcinol, 2-methylresorcinol, 3-aminophenol, and 5-amino-2-methylphenol. A majority of the shades have been produced with dyes based on p-phenylenediamine.

However, U.S. Pat. Nos. 5,599,353 and 5,538,516 describe that continued use of p-phenylenediamine is being questioned for toxicological reasons, mainly due to a strong sensitization potential. British patent publication GB 2,239,265A describes that some individuals (para-allergic persons) are being sensitized to p-phenylenediamine and its derivatives. In replacing p-phenylenediamine, EP 400,331 B1 and GB 2,239,205A describe the use of 2-(2-hydroxyethyl)-p-phenylenediamine. However, 2-(2-hydroxyethyl)-p-phenylenediamine is not sufficiently stable. The free base oxidizes and loses its dyeing ability over extended storage, even if stored in dark and sealed containers. Therefore, this compound is employed in its salt form. Additionally, the synthesis of 2-(2-hydroxyethyl)-p-phenylenediamine is relatively complex. Thus, the complexity of the synthesis procedure required, the necessity to convert the primary intermediate to its salt form, and its use in the salt form to formulate dyeing compositions adds unwanted expense and complexity to the production of hair coloring compositions. In the absence of the use of the compound in its salt form, reliable dyeing cannot be obtained if the free base form is utilized after extended periods of storage thereof.

Pyrimidine derivatives, such as tetraaminopyrimidine, have also been suggested as alternatives to p-phenylenediamine (see US Re. 30,199 [U.S. Pat. No. 4,003,699]). However, GB 2,239,265A points out that although the use of pyrimidine derivatives as developers has reduced toxicological problems, the pyrimidine derivatives are not completely satisfactory with respect to coloring performance.

U.S. Pat. No. 5,421,833 discloses hair dye compositions asserted to be without sensitizing potential. The dye compositions are disclosed to possess improved dyeing properties for all shades. The compositions comprise only 2-(2-hydroxyethyl)amino-5-aminotoluene in combination with the usual coupling agents (with the exclusion of 1-methoxy-2,4-diaminobenzene and 1-ethoxy-2,4-diaminobenzene).

BRIEF SUMMARY OF THE INVENTION

It is therefore an object of the present invention to provide a more suitable alternative to p-phenylenediamine as a primary intermediate in hair coloring compositions and systems.

It is a further object of this invention to provide a more suitable alternative to p-phenylenediamine as a primary intermediate that can be easily prepared and is more stable in the free base form than the intermediate 2-(2-hydroxyethyl)-p-phenylenediamine suggested in the aforementioned EP 400,330 B1 and GB 2,239,265A publications.

It has been discovered that the novel compound 1-(2,5-diaminophenyl)ethanol of the formula 1:

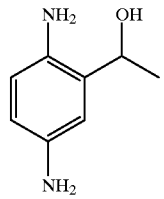

is easily prepared and is unexpectedly significantly more stable in its free base form than 2-(2-hydroxyethyl)-p-phenylenediamine and, therefore, provides a significantly improved primary intermediate for oxidative hair coloring compositions and systems. This novel primary intermediate is also much less susceptible to cause sensitization than p-phenylenediamine, i.e., it has a weaker sensitization potential.

This invention therefore provides this novel primary intermediate, a process for its production, and hair coloring compositions and systems employing this novel primary intermediate.

Whereas current technology generally requires p-phenylenediamine or p-toluenediamine for producing red and black shades (see U.S. Pat. No. 5,538,516), the present invention enables one skilled in the art to formulate a natural black shade and dark red shade through the use of 1-(2,5-diaminephenyl)ethanol without relying on p-phenylenediamine (see Tables 1 and 2). It is also advantageous that the shades obtained through use of 1-(2,5-diaminophenyl)ethanol have good wash, weather, and light fastness.

A process for the preparation of the 1-(2,5-diaminophenyl)ethanol is new and commercially feasible. The synthesis of 1-(2,5-diaminophenyl)ethanol can be accomplished by reduction of 1-(2-amino-5-nitrophenyl)ethanone to 1-(2-amino-5-nitrophenyl)ethanol and then hydrogenating the 1-(2-amino-5-nitrophenyl)ethanol to convert the nitro group to an amino group whereby 1-(2,5-diaminophenyl)ethanol is produced.

1-(2,5-Diaminophenyl)ethanol has excellent solubility in water. Water solubility is important because hair dye formulations employed for hair coloring are in large part water. Moreover, the free base evidences excellent long term storage stability.

The novel 1-(2,5-diaminophenyl)ethanol primary intermediate of this invention can be prepared from the known compound 1-(2-aminophenyl)ethanone as indicated previously or by a synthesis process starting from the known compound 1-(2-aminophenyl)ethanone 2 according to the following reaction scheme:

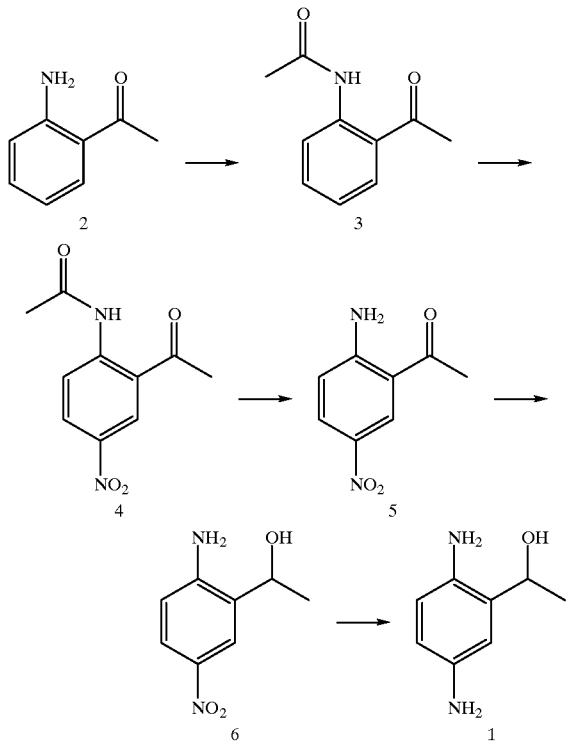

To 1-(2-amino-phenyl)-ethanone 2 (90.37 g, 0.67 moles) was added acetic anhydride (68.25 g, 0.67 moles) and stirred for 2 h at 4° C. The reaction mixture was poured into crushed ice and the precipitate was filtered, washed with ice water, and air-dried to afford N-(2-acetyl-phenyl)-acetamide 3 (104.70 g, 88% yield). $^1$HNMR (400 MHz, DMSO-$d_6$) δ2.10 (s, 3H), 2.60 (s, 3H), 7.17–7.21 (m, 1H), 7.55–7.59 (m, 1H), 7.95 (d, 1H, J=8.0 Hz), 8.26 (d, 1H, J=8.0 Hz), 11.16 (s 1H); MS m/z 17 (M$^+$).

The amide 3 (104.70, 0.59 moles) was added portion-wise over 0.5 h to a mixture of sulfuric acid (250 mL) and fuming nitric acid (250 mL) at 4° C. and stirred for another 1.5 h. The reaction mixture was poured into crushed ice and the precipitate filtered, washed with water, and air-dried to afford N-(2-acetyl-4-nitro-phenyl)-acetamide 4 (85.56 g, 65% yield). $^1$HNMR (400 MHz, DMSO-$d_6$) δ2.18 (s, 3H), 2.70 (s, 3H), 8.41–8.47 (m, 2H), 8.70 (dd, 1H, J=2.6, 10.4 Hz), 11.42 (s, 1H); MS m/z 222 (M$^+$).

A mixture of 4 (85.56 g, 0.39 moles) and 6 N HCl (600 mL) was stirred for 2 h at 80° C. The suspension was filtered, washed with water, and air-dried to afford 1-(2-amino-5-nitro-phenyl)ethanone 5 (54.95 g, 79% yield). $^1$HNMR(400 MHz, DMSO-$d_6$) δ2.61 (s, 3H), 6.86 (d, 1H, J=9.4 Hz), 8.07 (dd, 1H, J=2.6, 9.4 Hz), 8.61 (d, 1H, J=2.6), 8.08–8.61 (bs, 2H); MS m/z 180 (M$^+$).

To a stirred suspension of 5 (27.02 g, 150 mmole) in methanol (150 mL) at 4° C. was added sodium borohydride (5.67 g, 150 mmole) over a period of 0.25 h. After the addition was complete, the solution was warmed to room temperature and stirred for 0.25 h. The methanol was evaporated under vacuum. Water (150 mL) was added to the residue and the precipitate was filtered, washed with cold water, and air dried to afford 1-(2-amino-5-nitro-phenyl)-ethanol 6 (27.0 g, 99% yield). $^1$HNMR (400 MHz, DMSO-$d_6$) δ1.27 (d, 3H, J=6.3), 4.77–4.82 (m, 1H), 5.36 (d, 1H, J=4.3 Hz), 6.50 (s, 2H), 6.63 (d, 1H, J=9.0 Hz), 7.85 (dd, 1H, J=2.8, 9.0 Hz), 8.07 (d, 1H, J=2.6); MS m/z 182 (M$^+$).

Catalytic hydrogenation of 6 (27.0 g, 150 mmole) under 60 psi hydrogen pressure with 10% Pd/C (2.7 g) in anhydrous MeOH (150 mL)/ethyl acetate (150 mL) was completed in 2.5 h. The catalyst was removed by filtration over Celite. The filtrate was evaporated under vacuum to afford 1-(2,5-diamino-phenyl)-ethanol 1 (22.83 g, 100 % yield). Mp 124° C.; $^1$HNMR (400 MHz, DMSO-$d_6$) δ1.26 (d, 3H, J=6.4 Hz), 4.15 (d, 4H, J=10.7 Hz), 4.61–4.65 (m, 1H), 4.94 (d, 1H, J=3.6 Hz), 6.24 (dd, 1H, J=2.5, 8.2 Hz), 6.36 (d, 1H, J=8.2 Hz), 6.45 (d, 1H, J=2.5 Hz); MS m/z 152 (M$^+$); Anal. Calcd. for C8H12N2O: C, 63.13. H, 7.95. N, 18.41.O, 10.51. Found: C, 62.83. H, 7.90. N, 18.46. O, 10.17.

Hair coloring compositions of this invention can contain 1-(2,5-diaminophenyl)ethanol as the sole primary intermediate or can also contain other primary intermediates and couplers.

It should be noted that for certain dark shades, including dark brown and black shades, it is desirable to include a meta diamine as one of the couplers. Suitable meta diamines include m-phenylenediamine, 2,4-diaminophenoxyethanol and 4,6-bis(2-hydroxyethoxy)-m-phenylenediamine. For certain dark shades of red coloring, it is desirable to include 2-methyl-5-aminophenol as a coupler.

For hair coloring compositions of this invention, there may be used one or more other suitable primary intermediates other than the novel 1-(2,5-diaminophenyl)ethanol. Suitable other primary intermediates include, for example:

p-phenylenediamine derivatives such as: 2-methyl-p-phenylenediamine, p-phenylenediamine, 2-chloro-p-phenylenediamine, N-phenyl-p-phenylenediamine, N-(2-methoxyethyl)-p-phenylenediamine, N,N-bis(2-hydroxyethyl)-p-phenylenediamine, 2-hydroxymethyl-p-phenylenediamine, 2-(1-hydroxyethyl)-p-phenylenediamine, 2-(2-hydroxyethyl)-p-phenylenediamine, 4,4'diamino-diphenylamine, 2,6-dimethyl-p-phenediamine, 2-isopropyl-p-phenylenediamine, N-(2-hydroxypropyl)-p-phenylendiamine, 2-propyl-p-phenylenediamine, 1,3-bis[(N-hydroxyethyl)-N-(4-aminophenyl)amino]-2-propanol, 2-methyl-4-dimethylamino-aniline, 2-methoxy-p-phenylenediamine, 1-(2,5-diaminophenyl)-ethane-1,2-diol, 2,3-dimethyl-p-phenylenediamine, 2-(1,2-dihydroxyethyl)-p-phenylenediamine and 2-thiophen-2-yl-benzene-1,4-diamine, p-aminophenol derivatives such as: p-aminophenol, p-methylaminophenol, 3-methyl-4-aminophenol, 2-hydroxymethyl-4-aminophenol, 2-methyl-4-aminophenol, 2-(2'-hydroxyethylaminomethyl)-4-aminophenol, 2-methoxymethyl-4-aminophenol, 5-aminosalicylic acid, and 1-(5-amino-2-hydroxphenyl)-ethane-1,2-diol, o-aminophenol derivatives such as: o-aminophenol, 2,4-diaminophenol, 5-methyl-2-aminophenol, 6-methyl-2-aminophenol, 2-ethylamino-p-cresol and 2-amino-5-acetaminophenol, and 4-methyl-2-aminophenol, heterocyclic derivatives such as: 2,4,5,6-tetraaminopyrimidine, 4,5-diamino-1-methylpyrazole, 2-dimethylamino-5-aminopyridine, 1-(2-hydroxyethyl)-4,5-diaminopyrazole, 4-hydroxy-2,5,6-triaminopyrimidine, 2-(2-hydroxyethylamino)-6- methoxy-3-aminopyridine and 3-amino-2-methylamino-6-methoxypyridine,

The primary intermediates can be employed in the form of a free base or in the form of an acid additive salt thereof, such as, for example, as a hydrochloride, a hydrobromide, a sulfate or the like.

Suitable couplers include, for example:

phenols, resorcinol and naphthol derivatives such as: 1,7-dihydroxynaphthalene, resorcinol, 4-chlororesorcinol, 1-naphthol, 2-methyl-1-naphthol, 1-acetoxy-2-methylnaphthalene, 1,5-dihydroxynaphthalene, 2,7-dihydroxynaphthalene, hydroquinone, 2-methylresorcinol, 1-hydroxy-6-aminonaphthalene-3-sulfonic acid, 2-isopropyl-5-methylphenol, 1,5-dihydroxy-1,2,3,4-tetrahydronaphthalene, 2-chlororesorcinol, 2,3-dihydroxy-1,4-naphthoquinone and 1-naphthol-4-sulfonic acid, 1,2,3-trihydroxybenzene, m-phenylenediamines such as: m-phenylenediamine, 2,4-diamino-phenoxyethanol, N,N-bis(2-hydroxyethyl)-m-phenylenediamine, 2,6-diaminotoluene, 2-N,N-bis(hydroxyethyl)-2,4-diaminophenetole, 1,3-bis(2,4-diaminophenoxy)propane, 1-hydroxyethyl-2,4-diaminobenzene, 2-amino-4-(2-hydroxyethylamino)anisole, 4-(2-aminoethoxy)-1,3-diaminobenzene, 2,4-diaminophenoxyacetic acid, 4,6-bis(2-hydroxyethoxy)-m-phenylenediamine, 2,4-diamino-5-methylphenetole, 2,4-diamino-5-hydroxyethoxy-toluene, 2,4-dimethoxy-1,3-diaminobenzene and 2,6-bis(2-hydroxyethylamino)-toluene, 3-(2,4-diaminophenoxy)-1-propanol, m-aminophenols such as: m-aminophenol, 2-hydroxy-4-(carbamoylmethylamino)toluene, m-carbamoylmethylaminophenol, 6-hydroxybenzomorpholine, 2-hydroxy-4-aminotoluene, 2-hydroxy-4-(2-hydroxyethylamino) toluene, 4,6-dichloro-m-amino-phenol, 2-methyl-m-aminophenol, 2-chloro-6-methyl-m-aminophenol, 2-(2-hydroxyethoxy-5-aminophenol, 2-chloro-5-trifluoroethylaminophenol, 4-chloro-6-methyl-m-aminophenol, N-cyclopentyl-3-aminophenol, N-hydroxyethyl-4-methoxy-6-methyl-m-aminophenol and 5-amino-4-methoxy-2-methylphenol, heterocyclic derivatives such as: 1-phenyl-3-methyl-5-pyrazolone, 6-methoxy-8-aminoquinoline, 2,6-dihydroxy-4-methylpyridine, 5-hydroxy-1,4-benxodioxane, 3,4-methylenedioxyphenol, 4-(2-hydroxyethylamino)-1,2-methylenedioxybenzene, 2,6-dihydroxy-3,4-dimethylpyridine, 5-chloro-2,3-dihydroxpyridine, 3,5-diamino-2,6-dimethoxypyridine, 3,4-methylenedioxyaniline, 2,6-bis(2-hydroxyethoxy)-3,5-diaminopyridine, 4-hydroxyindole, 3-amino-5-hydroxy-2,6-dimethoxypyridine, 5,6-dihydroxyindole, 7-hydroxyindole, 5-hydroxyindole, 2-bromo-4,5-methylenedioxyphenol, 6-hydroxyindole, 2-amino-3-hydroxypyridine, 2,6-diaminopyridine, 5-(3,5-diamino-2-pyridyloxy)-1,3-dihydroxypentane, 3-(3,5-diamino-2-pyridyloxy)-2-hydroxypropanol and isatin.

Preferred primary intermediates include:

p-phenylenediamine derivatives such as: 2-methyl-p-phenylenediamine, p-phenylenediamine, N-(2-methoxyethyl)-p-phenylenediamine, N,N-bis(2-hydroxyethyl)-p-phenylenediamine, 2-(1-hydroxyethyl)-p-phenylenediamine, 2-(2-hydroxyethyl)-p-phenylenediamine, and 2-(1,2-dihydroxyethyl)-p-phenylenediamine, p-aminophenol derivatives such as: p-aminophenol, p-methylaminophenol, 3-methyl-4-aminophenol, 2-methoxymethyl-4-aminophenol, and 1-(5-amino-2-hydroxyphenyl)-ethane-1,2-diol, o-aminophenol derivatives such as: o-aminophenol, 2-ethylamino-p-cresol, 5-methyl-2-aminophenol, 6-methyl-2-aminophenol and 2-amino-5-acetaminophenol, 4-methyl-2-aminophenol, heterocyclic derivatives such as: 2,4,5,6-tetraaminopyrimidine 4,5-diamino-1-methylpyrazole, 1-(2-hydroxyethyl)-4,5-diaminopyrazole, and 2-dimethylamino-5-aminopyridine.

Preferred couplers include:

phenols, resorcinol and naphthol derivatives such as: 2-methyl-1-naphthol, 1-acetoxy-2-methylnaphthalene, 1,7-dihydroxynaphthalene, resorcinol, 4-chlororesorcinol, 1-naphthol, 1,5-dihydroxynaphthalene, 2,7-dihydroxynaphthalene, hydroquinone, 2-methylresorcinol and 2-isopropyl-5-methylphenol, m-phenylenediamines such as: m-phenylenediamine, 2,4-diaminophenoxyethanol, 1,3-bis(2,4-diaminophenoxy)propane, 2-amino-4-(2-hydroxyethylamino)anisole and 4,6-bis(2-hydroxyethoxy)-m-phenylenediamine, 3-(2,4-diaminophenoxy)-1-propanol, m-aminophenols such as: m-aminophenol, 6-hydroxybenzomorpholine, 2-hydroxy-4-aminotoluene, 2-hydroxy-4-(2-hydroxyethylamino)toluene and 2-methyl-m-aminophenol, heterocyclic derivatives such as: 1-phenyl-3-methyl-5-pyrazolone, 3,4-methylenedioxyphenol, 3,4-methylenedioxyaniline, 4-hydroxyindole, 5,6-dihydroxyindole, 7-hydroxyindole, 5-hydroxyindole, 6-hydroxyindole, isatin, 2,6-diaminopyridine and 2-amino-3-hydroxypyridine.

Most preferred primary intermediates include:

p-phenylenediamine derivatives such as: 2-methyl-p-phenylenediamine, p-phenylenediamine, N,N-bis(2-hydroxyethyl)-p-phenylenediamine and 2-(1-hydroxyethyl)-p-phenylenediamine and 2-(2-hydroxyethyl)-p-phenylenediamine, p-aminophenol derivatives such as: p-aminophenol, p-ethylaminophenol, 3-methyl-4-aminophenol and 1-(5-amino-2-hydroxyphenyl)-ethane-1,2-diol, o-amino derivatives such as: o-aminophenol, 2-ethylamino-p-cresol, 5-methyl-2-aminophenol, 6-methyl-2-aminophenol and 2-amino-5-acetaminophenol, heterocyclic derivatives such as: 2,4,5,6-tetraaminopyrimidine, 1-(2-hydroxyethyl)-4,5-diaminopyrazole.

Most preferred couplers include:

phenols, resorcinol and naphthol derivatives such as: 2-methyl-1-naphthol, 1-acetoxy-2-methylnaphthalene, resorcinol, 4-chlororesorcinol, 1-naphthol and 2-methylresorcinol, m-phenylenediamines such as: 2,4-diaminophenoxyethanol, 2-amino-4-(2-hydroxyethylamino)anisole and 4,6-bis(2-hydroxyethoxy)-m-phenylenediamine, and 3-(2,4-diaminophenoxy)-1-propanol, m-aminophenols such as: m-aminophenol, 6-hydroxybenzomorpholine, 2-hydroxy-4-aminotoluene, 2-hydroxy-4-(2-hydroxyethylamino) toluene and 2-methyl-m-aminophenol, heterocyclic derivatives such as: 1-phenyl-3-methyl-5-pyrazolone, 2-amino-3-hydroxypyridine and 6-hydroxyindole.

Preferred combinations employing 1-(2,5-diaminophenyl)ethanol as a p-phenylenediamine replacement include combinations as set forth in Tables 1 to 6 which follow.

The hair coloring compositions of this invention will generally contain the primary intermediate of this invention alone or in combination with other primary intermediates in an effective coloring amount, generally in an amount of from about 0.01 to about 3.5 weight percent. The coupler(s) will generally be present in an amount of from about 0.01 to about 2.5 weight percent. The molar ratio of primary intermediate to coupler will generally range from about 5:1 to about 1:5 and be employed in any suitable carrier or vehicle, generally an aqueous or hydroalcoholic solution, preferably an aqueous solution. The carrier or vehicle will generally comprise up to about 40 weight percent.

The hair coloring compositions of this invention may contain one or more cationic, anionic or amphoteric surface active agents, perfumes, antioxidants, sequestering agents, thickening agents, alkalizing or acidifying agents, and other dyeing agents.

Any suitable peroxide providing agent can be employed in the coloring compositions of this invention, particularly hydrogen peroxide ($H_2O_2$) or precursors therefor.

In general, a first composition of primary intermediate(s) and coupler(s) is prepared and then, at the time of use, the oxidizing agents, such as $H_2O_2$, is admixed therewith until an essentially homogenous composition is obtained which is applied to the hair to be dyed and permitted to remain in contact with the hair for a dyeing effective amount of time, generally for a period of from about 2 to 45, preferably about 2 to 30, minutes, after which the hair is rinsed, shampooed and dried.

The following compositions shown in Tables 1 to 4 are mixed with 100 g of 20 volume hydrogen peroxide. The resulting mixture is applied on gray hair and permitted to remain in contact with hair for 30 minutes. Thus, dyed hair is then shampooed and rinsed with water and dried. Hair coloration of good wash and light fastness was obtained.

TABLE 1

Dyeing Composition of Dark Red

|  | Composition (%) |
|---|---|
| Cocamidopropyl betaine | 17.00 |
| Ethanolamine | 2 |
| Oleic Acid | 0.75 |
| Citric Acid | 0.1 |
| Ammonium hydroxide | 5.0 |
| Behentrimonium chloride | 0.5 |
| Sodium sulfite | 0.1 |
| EDTA | 0.1 |
| Erythorbic acid | 0.4 |
| 1-(2,5-Diaminophenyl)ethanol | 2.66 |
| 4-Aminophenol | 0.924 |
| 2-Methyl-5-aminophenol | 1.54 |
| Water | QS 100 |
| Shade on gray hair | Dark Red |

TABLE 2

Dyeing Composition of Black Shade

|  | Composition (%) |
|---|---|
| Cocamidopropyl betaine | 15 |
| Ethanolamine | 3 |
| Ammonium hydroxide | 8.0 |
| Sodium sulfite | 0.1 |
| Citric acid | 10.0 |
| Erythorbic acid | 0.4 |
| 1-(2,5-Diaminophenyl)ethanol | 2.66 |
| N,N-Bis(2-hydroxyethyl)-p-phenylenediamine sulfate | 1.5 |
| Resorcinol | 2.0 |
| m-Aminophenol | 0.8 |
| 2,4-Diaminophenoxyethanol hydrochloride | 1.0 |
| Water | QS 100 |
| Shade on gray hair | Natural Black |

TABLE 3

Compositions for Dyeing Hair Red

| Ingredients | Example 1 WT % | Example 2 WT % | Example 3 WT % | Example 4 WT % | Example 5 WT % |
|---|---|---|---|---|---|
| Cocamidopropyl betaine | 17.00 | 17.00 | 17.00 | 17.00 | 17.00 |
| Ethanolamine | 2.00 | 2.00 | 2.00 | 2.00 | 2.00 |
| Oleic acid | 0.75 | 0.75 | 0.75 | 0.75 | 0.75 |
| Citric acid | 0.10 | 0.10 | 0.10 | 0.10 | 0.10 |
| Ammonium hydroxide | 5.00 | 5.00 | 5.00 | 5.00 | 5.00 |
| Behentrimonium chloride | 0.50 | 0.50 | 0.50 | 0.50 | 0.50 |
| Sodium sulfite | 0.10 | 0.10 | 0.10 | 0.10 | 0.10 |
| EDTA | 0.10 | 0.10 | 0.10 | 0.10 | 0.10 |
| Erythorbic acid | 0.40 | 0.40 | 0.40 | 0.40 | 0.40 |
| 1-(2,5-Diaminophenyl)ethanol | 2.00 | 2.00 | 1.50 | 0.30 | 0.30 |
| 4-Aminophenol | 0.92 |  |  | 2.50 | 2.50 |
| 3-Methyl-p-aminophenol |  | 1.20 |  |  |  |
| 2-Methyl-p-aminophenol |  |  | 1.75 |  |  |
| 2-Methyl-5-aminophenol | 1.54 |  | 1.60 | 1.00 | 1.00 |
| 2-Methyl-5-hydroxyethyl aminophenol |  | 0.75 |  |  |  |
| 2-Amino-5-methylphenol |  |  | 0.10 |  |  |
| 1-Naphthol |  |  |  | 1.50 |  |
| 2-Methyl-1-naphthol |  |  |  |  | 1.50 |
| Water | qs to 100 | qs to 100 | qs to 100 | qs to 100 | qs to 100 |

TABLE 3-continued

Compositions for Dyeing Hair Red

| Ingredients | Example 1 WT % | Example 2 WT % | Example 3 WT % | Example 4 WT % | Example 5 WT % |
|---|---|---|---|---|---|
| Color obtained on gray hair: | Dark Red | Burgundy Red | Bright Red | Bright Red | Bright Red |

TABLE 4

Compositions for Dyeing Hair Black to Brown

| Ingredients | Example 6 WT % | Example 7 WT % | Example 8 WT % | Example 9 WT % | Example 10 WT % |
|---|---|---|---|---|---|
| Cocamidopropyl betaine | 17.00 | 17.00 | 17.00 | 17.00 | 17.00 |
| Ethanolamine | 2.00 | 2.00 | 2.00 | 2.00 | 2.00 |
| Oleic acid | 0.75 | 0.75 | 0.75 | 0.75 | 0.75 |
| Citric acid | 0.10 | 0.10 | 0.10 | 0.10 | 0.10 |
| Ammonium hydroxide | 5.00 | 5.00 | 5.00 | 5.00 | 5.00 |
| Behentrimonium chloride | 0.50 | 0.50 | 0.50 | 0.50 | 0.50 |
| Sodium sulfite | 0.10 | 0.10 | 0.10 | 0.10 | 0.10 |
| EDTA | 0.10 | 0.10 | 0.10 | 0.10 | 0.10 |
| Erythorbic acid | 0.40 | 0.40 | 0.40 | 0.40 | 0.40 |
| 1-(2,5-Diaminophenyl)ethanol | 2.00 | 0.75 | 1.50 | 0.03 | 0.03 |
| N,N-Bis(2-hydroxyethyl)-p-phenylenediamine | 1.00 | 1.00 | 0.75 | | 0.05 |
| 1-(4-Aminophenyl)pyrrolidine | | 1.00 | | | |
| 4-Aminophenol | | | | 0.10 | 0.05 |
| 2-Aminophenol | | | | 0.10 | 0.10 |
| Resorcinol | 2.00 | 2.00 | | | |
| 2-Methylresorcinol | | | 1.00 | 0.20 | 0.20 |
| m-Aminophenol | 1.50 | 0.80 | 0.80 | 0.05 | 0.10 |
| 2,4-Diaminophenoxyethanol hydrochloride | | 0.50 | | | |
| 4,6-Bis(2-hydroxyethoxy)-m-phenylenediamine | 2.00 | | | | |
| 2-Amino-3-hydroxypyridine | | 0.50 | | | |
| 1-Naphthol | 1.00 | | | 0.03 | 0.02 |
| 2-Methyl-1-naphthol | | | 0.25 | | |
| Water | qs to 100 | qs to 100 | qs to 100 | qs to 100 | qs to 100 |
| Color obtained on gray hair: | Black | Dark Brown | Medium Brown | Golden Blonde | Ash Blonde |

The following dyeing compositions shown in Table 5 are mixed with 100 g of 20 volume hydrogen peroxide. The resulting mixture is applied on piedmont hair and permitted to remain in contact with hair for 30 minutes at 40° C. Thus, dyed hair is then shampooed and rinsed with water and dried. Hair coloration of good wash and light fastness was obtained.

TABLE 5

Dyeing Compositions

| Ingredients | Example 1 Weight % | Example 2 Weight % | Example 3 Weight % | Example 4 Weight % |
|---|---|---|---|---|
| Cocamidopropyl betaine | 17.0 | 17.0 | 17.01 | 17.0 |
| Monoethanolamine | 2.0 | 2.0 | 2.0 | 2.0 |
| Oleic acid | 0.75 | 0.75 | 0.75 | 0.75 |
| Citric acid | 0.1 | 0.1 | 0.1 | 0.1 |
| Ammonium hydroxide | 5.0 | 5.0 | 5.0 | 5.0 |
| Behentrimonium chloride | 0.5 | 0.5 | 0.5 | 0.5 |
| Sodium sulfite | 0.1 | 0.1 | 0.1 | 0.1 |
| EDTA | 0.1 | 0.1 | 0.1 | 0.1 |
| Erythorbic acid | 0.4 | 0.4 | 0.4 | 0.4 |
| Ethoxydiglycol | 3.5 | 3.5 | 3.5 | 3.5 |
| C1-15 Pareth-9 (Tergitol 15-S-9) | 1.0 | 1.0 | 1.0 | 1.0 |
| C12-15 Pareth-3 (Neodol 25-3) | 0.5 | 0.5 | 0.5 | 0.5 |
| Isopropanol | 4.0 | 4.0 | 4.0 | 4.0 |
| Propylene glycol | 2.0 | 2.0 | 2.0 | 2.0 |
| 1-(2-,5-Diaminophenyl)ethanol | 0.38 | 0.38 | 0.38 | 0.38 |
| 2,4-Diaminophenoxy-ethanol $H_2SO_4$ | 0.665 | | | |
| 2-Methyl-5-aminophenol | | 0.308 | | |
| Resorcinol | | | 0.275 | |
| 1-Naphthol | | | | 0.36 |
| Water | qs to 100 | qs to 100 | qs to 100 | qs to 100 |
| Color on Piedmont hair | Blue | Orange | Greenish yellow | Violet |

TABLE 6

| Structure | Name | 1 | 2 | 3 | 4 | 5 | 6 | 7 | 8 | 9 | 10 | 11 | 12 |
|---|---|---|---|---|---|---|---|---|---|---|---|---|---|
| 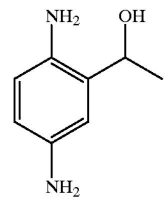 | 1-(2,5-Diamino-phenyl)-ethanol | X | X | X | X | X | X | X | X | X | X | X | X |
| 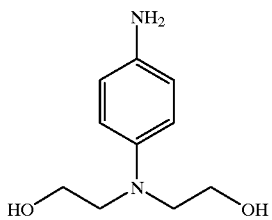 | 2-[(4-Amino-phenyl)-(2-hydroxy-ethyl)-amino]-ethanol | X | X | X | X | X | X | X | X | X | X | X | X |
| 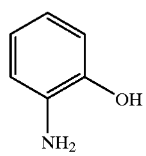 | 2-Amino-phenol | X | X | X | X | X | X | | | | | | |
| 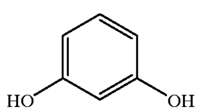 | Benzene-1,3-diol | X | | X | | X | | X | | X | | X | |
| 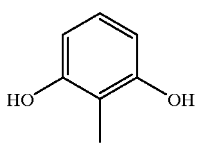 | 2-Methyl-benzene-1,3-diol | | X | | X | | X | | X | | X | | X |
| 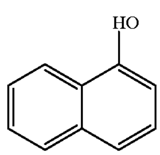 | Naphthalen-1-ol | X | | X | | X | | X | | X | | X | |
| 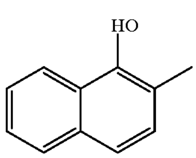 | 2-Methyl-naphthalen-1-ol | | X | | X | | X | | X | | X | | X |
| 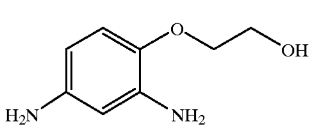 | 2-(2,4-Diamino-phenoxy)-ethanol | | | | | | | X | X | X | X | X | X |
| 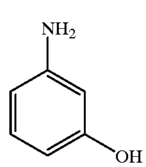 | 3-Amino-phenol | X | | X | | X | | X | | X | | X | |

TABLE 6-continued
| Structure | Name | | | | | | | | | | | | |
|---|---|---|---|---|---|---|---|---|---|---|---|---|---|
|  | 5-Amino-2-methyl-phenol | X | X | X | X | X | X | | | | | | |
| 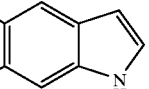 | 1H-Indole-5,6-diol | | | | | | | | | | | | |
| 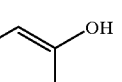 | 2-Amino-pyridin-3-ol | | | | | | | | | | | | |
|  | 4-Amino-phenol | X | X | | | X | X | | | | | | |
|  | 4-Amino-3-methyl-phenol | | | X | X | | | X | X | | | | |
| 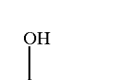 | 1-(5-Amino-2-hydroxy-phenyl)-ethane-1,2-diol | | | X | X | | | | | X | X | | |
| Structure | Name | 13 | 14 | 15 | 16 | 17 | 18 | 19 | 20 | 21 | 22 | 23 | 24 |
|---|---|---|---|---|---|---|---|---|---|---|---|---|---|
| | 1-(2,5-Diamino-phenyl)-ethanol | X | X | X | X | X | X | X | X | X | X | X | X |
| | 2-[(4-Amino-phenyl)-(2-hydroxy-ethyl)-amino]-ethanol | X | X | X | X | X | X | X | X | X | X | X | X |

TABLE 6-continued

| Structure | Name | | | | | | | |
|---|---|---|---|---|---|---|---|---|
| | 2-Amino-phenol | | | | | | | |
| | Benzene-1,3-diol | X | X | X | X | X | X | |
| | 2-Methyl-benzene-1,3-diol | | X | X | X | X | X | X |
| | Naphthalen-1-ol | X | X | X | X | X | X | |
| | 2-Methyl-naphthalen-1-ol | | X | X | X | X | X | X |
| | 2-(2,4-Diamino-phenoxy)-ethanol | | | | | | | |
| | 3-Amino-phenol | X | X | X | X | X | X | |
| | 5-Amino-2-methyl-phenol | | X | X | X | X | X | X |
| | 1H-Indole-5,6-diol | X | X | X | X | X | X | |
| | 2-Amino-pyridin-3-ol | | | | X | X | X | X | X | X |

TABLE 6-continued

| Structure | Compound | | | | | | |
|---|---|---|---|---|---|---|---|
| (4-aminophenol structure) | 4-Amino-phenol | X | X | | | X | X |
| (4-amino-3-methylphenol structure) | 4-Amino-3-methyl-phenol | X | X | | | X | X |
| (1-(5-amino-2-hydroxy-phenyl)-ethane-1,2-diol structure) | 1-(5-Amino-2-hydroxy-phenyl)-ethane-1,2-diol | | | X | X | X | X |

Preferred combinations employing 1-(2,5-diaminophenyl)ethanol as a p-phenylene diamine replacement include combinations 1–24 shown in Table 6. Reading down the columns in Table 6, the Xes demonstrate combinations of dyes that can be formulated according to the present invention. For example, in Column 5 of Table 6, the 1-(2,5-diaminophenyl)ethanol can be combined with 2-[(4-aminophenyl)-(2-hydroxyethyl)-amino]-ethanol, 2-aminophenol, benzene-1,3-diol, naphthalen-1-ol, 3-aminophenol and 1-(5-amino-2-hydroxy-phenyl)-ethane-1,2-diol.

With the foregoing description of the invention, those skilled in the art will appreciate that modifications may be made to the invention without departing from the spirit thereof. Therefore, it is not intended that the scope of the invention be limited to the specific embodiments illustrated and described.

We claim:

1. 1-(2,5-diaminophenyl)ethanol.

2. A process for the production of 1-(2,5-diaminophenyl) ethanol comprising:
  (a) providing 1-(2-amino-5-nitrophenyl)ethanone;
  (b) reducing 1-(2-amino-5-nitrophenyl)ethanone to 1-(2-amino-5-nitrophenyl)ethanol; and
  (c) hydrogenating 1-(2-amino-5-nitrophenyl)ethanol to convert the nitro group to an amino group whereby 1-(2,5-diaminophenyl)ethanol is produced.

3. A process according to claim 2 wherein the reduction is carried out with sodium borohydride as a reducing agent.

4. A process according to claim 3 wherein the hydrogenation is carried out with 10% Pd/C.

5. In a hair coloring system comprising a composition containing one or more oxidative hair coloring agents and a composition containing one or more oxidizing agents, the improvement comprising the presence of 1-(2,5-diaminophenyl)ethanol as a primary intermediate in the composition containing the one or more oxidative hair coloring agents.

6. A hair coloring system according to claim 5 wherein the composition comprising one or more oxidative hair coloring agents additionally comprises one or more primary intermediates selected from the group consisting of: 2-aminophenol, 4-aminophenol, 3-methyl-p-aminophenol, N,N-bis(2-hydroxyethyl)-p-phenylenediamine, 1-(4-aminophenyl) pyrrolidine, 2-hydroxyethyl-p-phenylenediamine, p-phenylenediamine and p-toluenediamine, 1-(2,5-diaminophenyl)ethane-1,2-diol, and 1-(5-amino-2-hydroxyphenyl)ethane-1,2-diol.

7. A hair coloring system according to claim 5 wherein the composition comprising one or more oxidative hair coloring agents additionally comprises one or more coupler selected from the group consisting of: 2-methyl-5-hydroxyethylaminophenol, 2-amino-5-methylphenol, 1-naphthol, 2-methyl-1-naphthol, resorcinol, 2-methylresorcinol, m-aminophenol, 2,4-diaminophenoxyethanol hydrochloride, 4,6-bis(2-hydroxyethoxy)-m-phenylenediamine, 2-amino-3-hydroxypyridine, 4-chlororesorcinol, 1-acetoxy-2-methylnaphthalane, m-phenylenediamine, 2,4-diaminophenoxyethanol, 2-amino-4-hydroxyethylamino anisole, and 2-hydroxy-4-aminotoluene.

8. In a system for coloring hair wherein at least one primary intermediate is reacted with at least one coupler in the presence of an oxidizing agent to produce an oxidative hair dye, the improvement wherein 1-(2,5-diaminophenyl) ethanol is employed as a primary intermediate.

9. A system for coloring hair according to claim 8 wherein the system additionally comprises one or more primary intermediates selected from the group consisting of: 2-aminophenol, 4-aminophenol, 3-methyl-p-aminophenol, N,N-bis(2-hydroxyethyl)-p-phenylenediamine, 1-(4-aminophenyl)pyrrolidine, 2-hydroxyethyl-p-phenylenediamine, p-phenylenediamine, and p-toluenediamine.

10. A system for coloring hair according to claim 8 wherein the system additionally comprises one or more couplers selected from the group consisting of: 2-methyl-5-hydroxyethylaminophenol, 2-amino-5-methylphenol, 1-naphthol, 2-methyl-1-naphthol, resorcinol, 2-methylresorcinol, m-aminophenol, 2,4-diaminophenoxyethanol hydrochloride, 4,6-bis(2-hydroxyethoxy)-m-phenylenediamine, 2-amino-3-hydroxypyridine, 4-chlororesorcinol, 1-acetoxy-2-methylnaphthalane, m-phenylenediamines, 2,4-diaminophenoxyethanol, 2-amino-4-hydroxyethylamino anisole, and 2-hydroxy-4-aminotoluene.

11. A system for coloring hair according to claim 8 wherein the system additionally comprises one or more primary intermediates selected from the group consisting of: 2-aminophenol, 4-aminophenol, 3-methyl-p-aminophenol, N,N-bis(2-hydroxyethyl)-p-phenylenediamine, 1-(4-aminophenyl)pyrrolidine, 2-hydroxyethyl-p-phenylenediamine, p-phenylenediamine, and p-toluenediamine and one or more couplers selected from the group consisting of: 2-methyl-5-hydroxyethylaminophenol, 2-amino-5-methylphenol, 1-naphthol, 2-methyl-1-naphthol, resorcinol, 2-methylresorcinol, m-aminophenol, 2,4-diaminophenoxyethanol hydrochloride, 4,6-bis(2-hydroxyethoxy)-m-phenylenediamine, 2-amino-3-hydroxypyridine, 4-chlororesorcinol, 1-acetoxy-2-methyinaphthalane, m-phenylenediamines, 2,4-diaminophenoxyethanol, 2-amino-4-hydroxyethylamino anisole, and 2-hydroxy-4-aminotoluene.

12. A hair coloring composition for dyeing human hair comprising, in a suitable carrier or vehicle, a dyeing effective amount of:
   (a) at least one primary intermediate comprising 1-(2,5-diaminophenyl)ethanol,
   (b) at least one coupler, and
   (c) at least one oxidizing agent.

13. A process for dyeing human hair comprising applying a dyeing effective amount of a hair coloring composition of claim 12 to the hair and permitting the composition to contact the hair for a dyeing effective period of time, and then rinsing, shampooing and drying the hair.

* * * * *